United States Patent [19]

Tronich et al.

[11] Patent Number: 4,990,673
[45] Date of Patent: Feb. 5, 1991

[54] PROCESS FOR THE PREPARATION OF 4,4'-DINITRODIPHENYLAMINE

[75] Inventors: Wolfgang Tronich, Eppstein/Taunus; Peter Hess, Hofheim am Taunus, both of Fed. Rep. of Germany

[73] Assignee: Hoechst Aktiengesellschaft, Frankfurt am Main, Fed. Rep. of Germany

[21] Appl. No.: 437,685

[22] Filed: Nov. 16, 1989

[30] Foreign Application Priority Data

Nov. 18, 1988 [DE] Fed. Rep. of Germany ....... 3839004

[51] Int. Cl.$^5$ ............................................ C07C 209/00
[52] U.S. Cl. .................................... 564/406; 560/339; 560/350; 564/433
[58] Field of Search ................ 564/433, 406; 560/339, 560/350

[56] References Cited

U.S. PATENT DOCUMENTS 3,055,940 9/1962 Merz .
4,670,596 6/1987 Dreikorn et al. .................... 564/433
4,709,087 11/1987 Tkatchenko et al. ............... 560/339

FOREIGN PATENT DOCUMENTS 1090225 10/1960 Fed. Rep. of Germany .
839420 6/1960 United Kingdom .

OTHER PUBLICATIONS

Gorvin, J. Chem. Soc. Perkin Trans. 1, 1988, pp. 1331–1335 (Chemical Abstracts, vol. 110 (1): 7744u).
McMurry, Organic Chemistry, 1984, p. 1159.
Gnehm, R. et al, Z. Angewandte Chemie 12: 1051–1055 (1899).

Primary Examiner—Richard L. Raymond
Assistant Examiner—Scott C. Rand

[57] ABSTRACT

Process for the preparation of 4,4'-dinitrodiphenylamine which comprises reacting 1 mole of 4-halonitrobenzene with about 1 to about 3 moles of an alkali metal cyanate in the presence of about 0.5 to about 5 moles of water in dimethylsulfoxide at temperatures of about 150° to about 170° C.

4 Claims, No Drawings

PROCESS FOR THE PREPARATION OF 4,4'-DINITRODIPHENYLAMINE

The invention relates to a process for the preparation of 4,4'-dinitrodiphenylamine which is an improvement over the prior art.

Using known processes 4,4'-dinitrodiphenylamine can be converted to 4,4'-diaminodiphenylamine, which is used as an intermediate for the preparation of dyestuffs, for example as a precursor for Colour Index Azoic Diazo Component 109, or for the preparation of antioxidants for rubber, oils and gasoline (DE-PS No. 1 090 225).

Several methods for the preparation of 4,4'-dinitrodiphenylamine have been disclosed hitherto:

Thus, 4,4'-dinitrodiphenylamine can be obtained by dinitration of N-acetyl-diphenylamine and subsequent deacetylation. An essential disadvantage of this process is that the nitration does not proceed uniformly and the isomeric nitrodiphenylamine compounds formed have to be removed by repeated recrystallizations from alcohol, both at the acetyl compound stage and also after the saponification of the acetyl compound at the free amine stage (Z. Angew. Chemie 12, 1051).

A process for the isomer-free preparation of 4,4'-dinitrodiphenylamine, which is an improvement on the above process, comprises, according to DE-PS No. 1 090 225, reacting 4-chloronitrobenzene, for example in the presence of dimethylformamide and copper salt catalysts, with 4-nitroaniline. However, despite a certain improvement, this process also is still subject to essential disadvantages.

Thus, required high reaction temperature of about 200° C. necessitates the use of expensive heating systems when the process is used industrially. Secondly, for ecological reasons, the copper compounds required as catalysts must be completely removed from the mother liquors by means of expensive separation processes and, finally, these production processes are tied to the use of 4-nitroaniline, which in turn must first be produced by reaction of 4-chloroaniline with ammonia.

Consequently there was still a requirement for a simple, ecologically acceptable process for the preparation of 4,4'-dinitrodiphenylamine.

It has now been found that 4,4'-dinitrodiphenylamine can be prepared in a simple manner by reacting 1 mole of 4-halonitrobenzene with about 1 to about 3 moles, preferably about 1.5 to about 2 moles, of an alkali metal cyanate in the presence of about 0.5 to about 5 moles, preferably about 1 to about 2 moles, of water in dimethylsulfoxide at temperatures of about 150° to about 170° C., preferably about 160° to about 165° C.

4-Chloronitrobenzene is the preferred 4-halonitrobenzene.

Sodium cyanate or potassium cyanate, preferably potassium cyanate, can be used as the alkali metal cyanate.

In principle there are no particular limits governing the quantity of the reaction medium dimethylsulfoxide. In general, however, it should be sufficient to maintain the reaction mixture in a stirrable condition.

The reaction time is between 15 and 24 hours, depending on the reaction temperature; in particular it is 16 to 20 hours at the preferred reaction temperature.

In principle the reaction can also be carried out in a closed reactor under the excess pressure established at the reaction temperature.

In general working up is effected by diluting the reaction mixture with water. In a preferred embodiment of the work-up the reaction mixture is introduced into up to 20 times the amount by weight of water and the precipitated reaction product is isolated. The dimethylsulfoxide can be recovered from the resulting mother liquor using customary methods, for example by means of fractional distillation.

Before being used further, the 4,4'-dinitrodiphenylamine obtained is generally subjected to a simple purification process, which, for example, consists in that the crude product is freed from residual 4-nitrochlorobenzene by brief treatment with steam and is then treated with dilute acid, e.g. mineral acid. In particular this can be effected by stirring the resulting crude product thoroughly with aqueous mineral acid, preferably aqueous hydrochloric acid and then isolating the product. By this means any 4-amino-nitrobenzene also formed will be dissolved out of the product. (4-Amino-nitrobenzene can then be precipitated from the aqueous mineral acid extract by addition of aqueous alkali hydroxide and then also isolated).

The process according to the invention is explained in more detail by the following examples, without being restricted to them.

EXAMPLE 1

79 parts by weight (0.5 mole) of 4-nitrochlorobenzene are heated with 82 parts by weight (1.0 mole) of potassium cyanate and 18 parts by weight (1.0 mole) of water in 200 parts by weight of dimethylsulfoxide for 20 hours at 160° to 165° C., with stirring. The cooled reaction mixture is then stirred into water and the precipitated reaction product is isolated by filtration. The moist product is treated with steam, approximately 2 parts by weight of 4nitrochlorobenzene distilling off. Aqueous hydrochloric acid is added to the residue at about 40° C., the mixture is stirred briefly, and the product is filtered off with suction and dried.

46.5 parts by weight (0.18 mole) of 4,4'-dinitrodiphenylamine are obtained, corresponding to a yield of 72% of theory (m.p.: 206° to 208° C.).

The pH of the filtrate is adjusted to 7 to 8 by the addition of aqueous sodium hydroxide solution and the precipitated 4-nitroaniline is filtered off and dried. About 10 parts by weight of 4-nitroaniline are obtained.

If 1 mole of sodium cyanate is used instead of 1 mole of potassium cyanate, markedly lower yields of 4,4'-dinitrodiphenylamine are then obtained.

EXAMPLE 2

The procedure is as in Example 1 except that 62 parts by weight (0.75 mole) of potassium cyanate and 14 parts by weight (0.75 mole) of water are used per 79 parts by weight (0.5 mole) 4-nitrochlorobenzene. After working up according to Example 1, 40 parts by weight (0.15 mole) of 4,4'-dinitrodiphenylamine are obtained, corresponding to a yield of 60% of theory (m.p.: 204° to 206° C.).

EXAMPLE 3

The procedure is as in Example 1 except that 82 parts by weight (1.0 mole) of potassium cyanate and 9 parts by weight (0.5 mole) of water are used per 79 parts by weight (0.5 mole) of 4-nitrochlorobenzene. The result corresponds to that of Example 1.

EXAMPLE 4

(Catalytic, reduction of 4,4'-dinitrodiphenylamine)

52 parts by weight (0.2 mole) of 4,4'-dinitrodiphenylamine are reduced in 250 parts by weight of methanol and in the presence of 4 parts by weight of active carbon as well as 2 parts by weight of disodium hydrogen phosphate on 6 parts by weight of 5% nickel catalyst on active carbon (e.g. of the type RCH 55/5 from Ruhrchemie AG) in the course of 45 minutes at a hydrogen pressure of up to 40 bar and a temperature rising up to 140° C. On completion of the reduction, the catalyst is filtered from the reaction mixture whilst still hot and the filtrate stirred directly into about 400 parts by weight of about 5 % aqueous sulfuric acid. The mixture is stirred until cooled to about 20° C., and the product is filtered off with suction and washed with water. 54 parts by weight of 4,4'-diaminodiphenylamine sulfate are obtained, corresponding to a yield of 91% of theory. The sulfate salt can be converted to 4,4'-diaminodiphenylamine by treatment with aqueous alkali metal hydroxide.

We claim:

1. A process for the preparation of 4,4'-dinitrodiphenylamine which comprises reacting 1 mole of 4-chloronitrobenzene with about 1 to about 3 moles of potassium cyanate in the presence of about 0.5 to about 5 moles of water in dimethylsulfoxide at temperatures of about 150° C. to about 170° C.

2. A process as claimed in claim 1, wherein 1 mole of 4-chloro-nitrobenzene is reacted with about 1.5 to about 2 moles of potassium cyanate in the present of about 1 to about 2 moles of water.

3. A process as claimed in claim 1,
   wherein the reaction is carried out at temperatures of about 160° to about 165° C.

4. A process as claimed in claim 1,
   wherein the reaction is carried out in an amount of dimethylsulfoxide which is at least such that the reaction mixture remains stirrable.

* * * * *